US007083795B1

(12) United States Patent
Sanhueza et al.

(10) Patent No.: US 7,083,795 B1
(45) Date of Patent: Aug. 1, 2006

(54) INACTIVATED RESPIRATORY SYNCYTIAL VIRAL VACCINES

(75) Inventors: Sonia E. Sanhueza, Willowdale (CA); Mary E. Ewasyshyn, Willowdale (CA); Michel H. Klein, Willowdale (CA)

(73) Assignee: Sanofi Pasteur Limited, Toronto (CA)

( * ) Notice: Subject to any disclaimer, the term of this patent is extended or adjusted under 35 U.S.C. 154(b) by 0 days.

(21) Appl. No.: 08/583,124

(22) PCT Filed: Aug. 4, 1994

(86) PCT No.: PCT/CA94/00425

§ 371 (c)(1), (2), (4) Date: Jun. 28, 1996

(87) PCT Pub. No.: WO95/04545

PCT Pub. Date: Feb. 16, 1995

Related U.S. Application Data

(63) Continuation-in-part of application No. 08/102,742, filed on Aug. 6, 1993, now abandoned.

(51) Int. Cl.
*A61K 39/155* (2006.01)

(52) U.S. Cl. .................................................. 424/211.1

(58) Field of Classification Search ............ 424/211.1; 435/238, 948, 235.1–239; 530/403, 412–414, 530/416, 417

See application file for complete search history.

(56) References Cited

U.S. PATENT DOCUMENTS

| | | | | |
|---|---|---|---|---|
| 4,591,505 | A * | 5/1986 | Prince | 424/101 |
| 4,664,912 | A | 5/1987 | Wiktor et al. | 424/89 |
| 4,732,683 | A * | 3/1988 | Georgiades et al. | 210/635 |
| 5,071,758 | A * | 12/1991 | Stott et al. | 435/240.2 |
| 5,200,179 | A * | 4/1993 | Bordt et al. | 424/89 |
| 5,223,254 | A * | 6/1993 | Paradiso et al. | 424/89 |

FOREIGN PATENT DOCUMENTS

| | | | |
|---|---|---|---|
| EP | 222415 | | 11/1986 |
| EP | 310317 | | 9/1988 |
| WO | 91 00104 | | 1/1991 |
| WO | 91/00104 | * | 1/1991 |
| WO | 93 21310 | | 10/1993 |

OTHER PUBLICATIONS

Kuchler, R.J.: Virus growth and purification: Biochem. Meth. in Cell Culture and Vir. : pp. 168-205, 1977.*
Mbiguino, et al.: Purification of human respiratory syncytial virus . . . : J. of Vir. Meth.: 31: pp. 161-170, 1991.*
Preston, et al.: Infectious respiratory syncytial virus (RSV) effectively . . . : JID: 165: pp. 819-825,1992.*
White, et al.: In vitro effect of ascorbic acid on infectivity . . . : J. of Clin. Micorbio.: pp. 527-531, 1986.*
McIntosh, et al.: Respiratory Syncytial Virus: Field's Virology: 2nd Ed.:pp. 1045-1072, 1990.*
Mbiguino, et al.: Purification of human respiratory syncytial virus. . . : J. of Vir. Meth. :31: pp. 161-170, 1991.*
White, et al: In vitro effect ascorbic acid on infectivity. . . : J. of Clin. Microbio.: pp. 527-531, 1986.*
McIntosh, et al.: Respiratory Syncytial Virus: Fields's Virology: 2nd Ed.: pp. 1045-1072, 1990.*
Downing, et al. : Active respiratory syncytial virus. . . : J. Vir. Meth.: 38: pp. 215-228, 1992.*
Hall, C.B., 1994, "Prospects for a respiratory syncytial virus vaccine", Science 265:1391-1394.*
Tristram, D.A., et al., 1993, "Respiratory syncytial virus vaccines: can we improve on nature?", Ped. Ann. 22:715-718.*

(Continued)

*Primary Examiner*—J. S. Parkin
(74) *Attorney, Agent, or Firm*—Sim & McBurney

(57) ABSTRACT

An immunogenic composition capable of producing a respiratory syncytial (RS) virus specific immune response in a host immunized therewith comprises purified, inactivated RS virus which is substantially free from cellular and serum components and which is non-infectious, non-immunopotentiating, immunogenic and protective. The virus is grown on a vaccine quality cell line and harvested virus is purified under non-denaturing conditions to be substantially free from cellular and serum components. The purified RS virus is inactivated using β-propiolactone, a non-ionic detergent, particularly n-octyl-α-D-glucopyranoside and n-octyl-β-D-glucopyranoside, or ascorbic acid. The immunogenic composition may be formulated as a vaccine for in vivo administration to a human host. The immunogenic composition also may be used in diagnostic applications.

5 Claims, No Drawings

OTHER PUBLICATIONS

Toms, G.L., 1995, "Respiratory syncytial virus—how soon will we have a vaccine?", Archiv. Dis. Child. 72:1-3.*
Murphy, B.R., et al., 1994, "An update on approaches to the development of respiratory syncytial virus (RSV) and parainfluenza virus type 3 (PIV) vaccines", Vir. Res. 32:13-36.*
Salkine, A.R. and N.J. Roberts, Jr., 1992, "Recent observations regarding the pathogenesis of recurrent respiratory syncytial virus infections: implications for vaccine development", Vaccine 10(8):519-523.*
Glezen, W.P., Paredes, A. Allison, J.E., Taber, L.H. and Frank, A.L. (1981). J. Pediatr. 98, 708-715.
Chanock, R.M., Parrot, R.H., Connors, M., Collins, P.L. and Murphy, B.R. (1992) Pediatrics 90, 137-142.
Martin, A. J., Gardiner, P.S. and McQuillin, J. (1978). Lancet ii, 1035-1038.
Robbins, A., and Freeman, P. (1988) Sci. Am. 259, 126-133.
Glezen, W.P., Taber, L.H., Frank, A.L. and Kasel, J.A. (1986) Am. J. Dis. Child. 140, 543-546.
Katz, S.L. New vaccine development establishing priorities. vol. 1. Washington: National Academic Press. (1985) pp. 397-409.
Wertz, G.W., Sullender, W.M. (1992) Biotech. 20, 151-176.
McIntosh, K. and Chanock, R.M. (1990) in Fields Virology (Fields, B.M., and Knipe, D.M. eds.) pp. 1045-1075, Raven Press, Ltd., New York.
Walsh, E.E., Hall, C.B., Briselli, M., Brandiss, M.W. and Schlesinger, J.J. (1987) J. Infect. Dis. 155, 1198-1204.
Walsh, E.E., Hruska, J. (1983) J. Virol. 47, 171-177.
Levine, S., Kleiber-France, R., and Paradiso, P.R. (1987) J. Gen. Virol. 69, 2521-2524.
Anderson, L.J., Hierholzer, J.C., Tsou, C., Hendry, R.M., Fernie, B.F., Stone, Y. and McIntosh, K. (1985),J. Infect. Dis. 151, 626-633.
Johnson, P.R., Olmsted, R.A., Prince, G.A., Murphy, B.R., Alling, D.W., Walsh, E.E. and Collins, P.L. (1987) J. Virol. 61 (10), 3163-3166.
Fulginiti, V.A., Eller, J.J., Sieber, O.F., Joyner, I.W., Minamitani, M. and Meiklejohn, G. (1969) Am. J. Epidemiol. 89 (4), 435-448.
Chin, J., Magoffin, R.L., Shearer, L.A., Schieble, J.H. and Lennette, E.H. (1969) Am. J. Epidemiol. 89 (4), 449-463.
Kapikian, A.Z., Mitchell, R.H., Chanock, R.M., Shvedoff, R.A. and Stewart, C.E. (1969) Am. J. Epidemiol. 89 (4), 405-421.
Kim, H.W., Arrobio, J.O., Pyles, G., Brandt, C.D Camargo, E., Chanock, R.M. and Parrott, R.H. (1971 Pediatrics 48, 745-755.
Wright, P.F., Belshe, R.B., Kim, H.W., Van Voris, L.P. and Chanock, R.M. (1982) Infect. Immun. 37 (1), 397-400.
Wright, P.F., Chinozaki, T. and Fleet, W. (1976) J. Pediatr. 88, 931-936.
Belshe, R.B., Van Voris, L.P. and Mufson, M.A. (1982) J. Infect. Dis. 145, 311-319.
Murphy, BR., Prince, G.A., Walsh, E.E, Kim H.W., Parrott, R.H., Hemming V.G., Rodriguez, W.J., and Chanock. J. Clin. Microbiol. (1986), 24 (2), 197-202.
Connors, M., Collins, P.L., Firestone, C-Y., Sotnikov, A.V., Waitze, A., Davis, A.R., Hung, P.P., Chanock R.M., Murphy, B. (1992) Vaccine, 10, 475-484.
Prince, G.A., Jenson, A.B., Hemming, V.G., Murphy, E.R., Walsh, E.E., Horswood, R.L and Chanock, R.L. (1986 b) J. Virol. 57 (3), 721-728.
Piedra, P.A., Camussi, F. and Ogra, P.L. (1989) J. Gen. Virol. 70, 325-333.
Prince et al, J. Virol 61,6 1851-1854, Jun. 1987.
Hemming V.G. et al, J. Infect. Dis., 152:1083-1087 (1985).
Budowsky, E.I. and Zheleznova, N.V. (1991) Vaccine 9 (6), 319-325.
Budowsky, E.I., Friedman, E.A., Zheleznova, N.V. and Noskov, F.S. (1991) Vaccine 9 (6), 398-402.
Stephan, W., Dichtelmuller, H., Prince, A.M., Brotman, B. and Huima, T. J. Med. Virol. (1988), 26 (3), 227-232.
Barth, R., Gruschkau, H., Bijok, U., Hilfenhaus, J., Hinz, J. and Milcke, L. J. Biol. Stand. (1994) , 12 (1), 29-46.
Salkind, A.R. and Roberts N.J. (1992) Vaccine. 10, 519-523.
Murphy, B.R., Prince, G.A., Collins, P.L. Coelingh, K.V.W., Olmsted R.A., Spriggs, M.K., Parrott, R.H., Kim, H-W., Brandt, C.D. and Chanock, R.M. (1988) Virus Research 11, 1-15.
Kimman, T.G. and Westenbrink, F. (1990) Archives of Virology 112, 1-25.
Wertz, G.W. and Sullender, W.M. (1992) Biotechnology 20: 151-176.
La Via, W.V., Marks, M.I., Stutman H.R. (1992) J. Pediatrics 121, 503-510.
Collins et al, Vaccine 8 (2) : 164-168, 1990.
Preston et al, Journal of Infectious Disease 165 (5) 819-825, 1992.
Mbiguino et al, Journal of Virological Methods 31:161-170, 1991.
Downing et al, Journal of Virological Methods 32:215-228, 1992.
Hall C.B., Science 265:1393-1394, 1994.
White et al, Journal of Clinical Microbiology, vol. 24, No. 4:527-531 1986.
Murphey-Corb et al., Vaccines 90: Mod. Approaches New Vaccines Incl. Prev. AIDS, [Conf.], 7$^{th}$ (1990), Meeting Date 1989, 393-9. Editor(s): Brown, Fred. Publisher: Cold Spring Harbor Lab., Cold Spring Harbor, NY.
Kuchler R.J., Biochemical Methods in Cell Culture & Virology, Dowden, Hutchingon & Ross, Inc. Stroudsburg, PA 168-205, 1977.
Groothuis et al (N. Engl. J. Med. 329:1524-1530).
Bissell et al, 1980, PNAS USA, 77:2711-2715.
Solo et al, 1978, App. Env. Microbiol 36:68-75.
Coe, J.E. and Prince, G.A.—Immunology 1996, 88, pp. 323-330.

* cited by examiner

INACTIVATED RESPIRATORY SYNCYTIAL VIRAL VACCINES

REFERENCE TO RELATED APPLICATION

This application is a national United States patent filing of PCT/CA94/00425 filed Aug. 4, 1994 which is a continuation-in-part of U.S. patent application Ser. No. 08/102,742 filed Aug. 6, 1993 (now abandoned).

FIELD OF THE INVENTION

The present invention is directed to the field of immunology and, in particular, to inactivated respiratory syncytial (RS) virus vaccines.

BACKGROUND OF THE INVENTION

Human respiratory syncytial virus is the main cause of lower respiratory tract infections among infants and young children (refs. 1 to 3—a list of references appears at the end of the disclosure and each of the references in the list is incorporated herein reference thereto). Globally, 65 million infections occur every year resulting in 160,000 deaths (ref. 4). In the USA alone, 100,000 children may require hospitalization for pneumonia and bronchiolitis caused by RS virus in a single year (refs. 5, 6). Providing inpatient and ambulatory care for children with RS virus infections costs in excess of $340 million annually in the USA (ref. 7). Severe lower respiratory tract disease due to RS virus infection predominantly occurs in infants two to six months of age (ref. 8). Approximately 4,000 infants in the USA die each year from complications arising from severe respiratory tract disease caused by infection with RS virus and Parainfluenza type 3 virus (PIV-3). The World Health Organization (WHO) and the National Institute of Allergy and Infectious Disease (NIAID) vaccine advisory committees have ranked RS virus second only to HIV for vaccine development.

RS virus is a member of the Paramyxoviridae family of the pneumovirus genus (ref. 2). The two major protective antigens are the envelope fusion (F) and attachment (G) glycoproteins (ref. 9). The F protein is synthesized as a 68 kDa precursor molecule (F0) which is proteolytically cleaved into disulfide-linked F1 (48 kDa) and F2 (20 kDa) polypeptide fragments (ref. 10). The G protein (33 kDa) is heavily O-glycosylated giving rise to a glycoprotein of apparent molecular weight of 90 kDa (ref. 11). Two broad subtypes of RS virus have been defined: A and B (ref. 12) The major antigenic differences between these subtypes are found in the G glycoprotein (refs. 7, 13).

A safe and effective RS virus vaccine is not available and is urgently needed. Approaches to the development of RS virus vaccines have included inactivation of the virus with formaldehyde, isolation of cold-adapted and/or temperature-sensitive mutant viruses and isolation of the protective antigens of the virus. Clinical trial results have shown that both live attenuated and formalin-inactivated vaccines failed to adequately protect vaccinees against RS virus infection (refs. 14 to 16). Problems encountered with cold-adapted and/or temperature-sensitive RS virus mutants administered intranasally included clinical morbidity, genetic instability and overattenuation (refs. 17 to 19). A live RS virus vaccine administered subcutaneously also was not efficacious (ref. 20). Inactivated RS viral vaccines have typically been prepared using formaldehyde as the inactivating agent. Murphy et al. (ref. 21) has reported data on the immune response in infants and children immunized with formalin-inactivated RS virus. Infants (2 to 6 months of age) developed a high titre of antibodies to the F glycoprotein but had a poor response to the G protein. Older individuals (7 to 40 months of age) developed titres of F and G antibodies comparable to those in children who were infected with RS virus. However, both infants and children developed a lower level of neutralizing antibodies than did individuals of comparable age with natural RS virus infections. The unbalanced immune response, with high titres of antibodies to the main immunogenic RS virus proteins F (fusion) and G (attachment) proteins but a low neutralizing antibody titre, may be in part due to alterations of important epitopes in the F and G glycoproteins by the formalin treatment. Furthermore, some infants who received the formalin-inactivated RS virus vaccine developed a more serious lower respiratory tract disease following subsequent exposure to natural RS virus than did non-immunized individuals (refs. 15, 16). The formalin-inactivated RS virus vaccines, therefore, have been deemed unacceptable for human use.

Evidence of an aberrant immune response also was seen in cotton rats immunized with formalin-inactivated RS virus (ref. 22). Furthermore, evaluation of RS virus formalin-inactivated vaccine in cotton rats also showed that upon live virus challenge, immunized animals developed enhanced pulmonary histopathology (ref. 23).

The mechanism of disease potentiation caused by formalin-inactivated RS virus vaccine preparations remains to be defined but is a major obstacle in the development of an effective RS virus vaccine. The potentiation may be partly due to the action of formalin on the F and G glycoproteins. Additionally, a non-RS virus specific mechanism of disease potentiation has been suggested, in which an immunological response to contaminating cellular or serum components present in the vaccine preparation could contribute, in part, to the exacerbated disease (ref. 24). Indeed, mice and cotton rats vaccinated with a lysate of HEp-2 cells and challenged with RS virus grown on HEp-2 cells developed a heightened pulmonary inflammatory response.

Furthermore, RS virus glycoproteins purified by immunoaffinity chromatography using elution at acid pH were immunogenic and protective but also induced immunopotentiation in cotton rats (refs. 22, 25).

There clearly remains a need for immunogenic preparations, including vaccines which are not only effective in conferring protection against disease caused by RS virus but also does not produce unwanted side-effects, such as immunopotentiation. There is also a need for antigens for diagnosing RSV infection and immunogens for the generation of antibodies (including monoclonal antibodies) that specifically recognize RSV proteins for use, for example, in diagnosis of disease caused by RS virus.

Art recognized approaches to the developments of RSV vaccines have been summarized in recent review articles (refs. 2, 31 to 34), none of which propose the development of an inactivated RSV vaccine.

SUMMARY OF THE INVENTION

The present invention provides a novel approach to the provision of such antigens and immunogens by inactivation of purified RS virus.

In one aspect of the present invention, there is provided a method of preparing an immunogenic composition capable of producing a respiratory syncytial (RS) virus specific immune response in a host immunized therewith, particularly a human host, which comprises a plurality of steps. The RS virus first is grown on an appropriate cell line and the virus harvested. The harvested virus is purified under non-denaturing conditions to produce a purified virus substantially free from cellular and serum components. The purified virus then is inactivated with an inactivating agent to provide a non-infectious, non-immunopotentiating and immunogenic RS virus. This RS virus then is formulated as an immunogenic composition.

The inactivating agent may be β-propiolactone; a non-ionic detergent, including n-octyl-α-D glucopyranoside and n-octyl-β-D-glucopyranoside; or ascorbic acid.

The purifying step which is carried out on the harvested virus preferably may be effected by microfiltration to remove cell debris, tangential flow ultrafiltration to remove serum components, particularly employing an about 100 to about 300 kDa nominal molecular weight cut-off membrane, pelleting the ultrafiltered material by ultracentrifugation to further remove serum components and subjecting the pelleted material to sucrose density gradient centrifugation. Alternatively, the retentate from tangential flow ultrafiltration may be subjected to gel filtration followed by ion-exchange chromatography to further remove serum components.

This procedure provides a novel immunogenic composition capable of producing an RS virus specific immune response in a host immunized therewith which constitutes a further aspect of the present invention. Such immunogenic composition comprises purified, inactivated RS virus which is substantially free from cellular and serum components and which is non-infectious, non-immunopotentiating, immunogenic and protective, and a carrier therefor. The immunogenic composition may be formulated as a vaccine for in vivo administration to a human host for protecting the human from a disease induced by RS virus. The carrier for the immunogenic composition may comprise an adjuvant. The immunogenic composition may be formulated as a vaccine to be administered in an injectable form, intranasally or orally.

The present invention further provides a method of immunizing a host, particularly a human host, against disease caused by RS virus, which comprises administering to the host an effective amount of the immunogenic composition provided herein. The host immunized by such procedure may be selected from infants, young children, pregnant women, women of childbearing age, elderly individuals, immunocompromised individuals and other susceptible persons.

The inactivated RS virus provided herein also may be used as a diagnostic reagent for detecting infection by RS virus. Accordingly, the present invention further includes a method of determining the presence of antibodies specifically reactive with RS virus proteins in a sample, comprising the steps of:

(a) contacting the sample with the immunogenic composition of the invention to produce complexes comprising the non-infectious, non-immunogenic and immunogenic RS virus and any antibodies present in the sample specifically reactive therewith; and (b) determining production of the complexes.

In addition, the present invention provides a method of determining the presence of RS virus proteins in a sample, comprising the steps of:

(a) immunizing a subject with the immunogenic composition of the invention to produce antibodies specific for RS virus proteins;

(b) contacting the sample with the antibodies to produce complexes comprising any RS virus proteins present in the sample and the RS virus protein-specific antibodies; and (c) determining production of the complexes.

The present invention further provides a diagnostic kit for determining the presence of antibodies in a sample specifically reactive with RS virus proteins, comprising:

(a) the immunogenic composition of the invention;

(b) means for contacting the non-infectious, non-immunopotentiating and non-immunogenic RS virus with the sample to produce complexes comprising the non-infectious, non-immunopotentiating and immunogenic RS virus and any said antibodies present in the sample; and (c) means for determining production of the complexes.

Having regard to the prior art difficulty with RS virus vaccine preparations, it is surprising that the procedures described herein provide immunogenic compositions which exhibits immunogenicity and protective ability while being non-infectious and non-immunopotentiating.

DETAILED DESCRIPTION OF THE INVENTION

In one aspect, the present invention relates to the preparation of an inactivated respiratory syncytial virus under conditions acceptable for use in human vaccines. RS virus, subtypes A or B, are grown in tissue culture in controlled fermenters on a vaccine quality cell line, which may particularly be VERO cells. Following harvesting of the virus, the virus is purified and then inactivated to produce an inactivated RS virus vaccine.

Growth of Cells

Vaccine quality cell lines, such as African green monkey kidney (VERO) cells, generally are grown on microcarrier beads (Cytodex-1). Such beads generally are swollen in a buffered solution, such as phosphate buffered saline (PBS), pH about 6.9 to about 8.2, without calcium and magnesium, for 2 to 4 hours at room temperature with gentle agitation (30 to 50 rpm). Washed beads are sterilized at 110° C. to 130° C. for 30 to 60 min, and conditioned in a cell culture medium, such as CMRL 1969, in spinner flasks or small (2 to 10L) or large (20 to 2000L) controlled fermenters. The vessel then is seeded (for example, $0.5\times10^5$ to $2\times10^5$ cells/mL) with vaccine quality VERO cells in a culture medium, such as CMRL 1969 supplemented with fetal bovine serum (FBS).

RS Virus Growth

Once the cells are approximately 80 to 90% confluent (3 to 5 days post-cell seeding), the culture supernatant is decanted and the cells washed once with a culture medium, such as CMRL 1969. The cells then are infected with RS virus in CMRL 1969 in the absence of FBS. After virus adsorption, the infected cells are washed in culture medium and virus growth is monitored for 5 to 7 days post-infection.

Virus Processing and Concentration

The harvested virus then is purified under non-denaturing conditions to be substantially free from cellular and serum components. Such purification may be effected in any convenient manner. In one such procedure, the RS virus supernatant is microfiltered (0.22 to 8 μm pore size filters) to remove cell debris. The clarified viral fluid then may be concentrated by tangential flow ultrafiltration using an ultrafiltration membrane with a molecular weight cut-off between about 100 to about 300 kDa, to remove serum components.

The concentrated RS virus is subjected to further purification for utilization in the immunogenic preparations and as antigens. In one procedure, the concentrated virus may be pelleted by ultracentrifugation and the supernatant from the ultracentrifugation is discarded thereby further removing serum components. The pelleted virus is resuspended in PBS or another suitable medium. The concentrated virus then is purified by sucrose density gradient ultracentrifugation. Alternatively, the retentate from the tangential flow ultrafiltration step may be subjected to gel filtration followed by ion-exchange chromatography to further remove serum components. The resulting RS viral material may be further pelleted by ultracentrifugation. The pelleted-purified RS virus may be resuspended in PBS and stored at −70° C. pending use.

Virus Inactivation

The purified RS virus next is inactivated. Such inactivation is effected using materials which provide the purified virus in a non-infectious, non-immunopotentiating and immunogenic form. The inactivating agent employed in this step generally comprises β-propiolactone, ascorbic acid or a non-ionic detergent. Among the non-ionic detergents which may be employed in the inactivation step are certain glucopyranosides, including n-octyl-β-D-glucopyranoside and n-octyl-α-D-glucopyranoside.

Any convenient quantity of inactivating agent and any desired reaction conditions may be employed consistent with the desire to provide a non-infectious, non-immunopotentiating and immunogenic material.

As an example, RS virus may be inactivated using about a 0.1% solution of β-propiolactone (BPL) for about 30 to 120 minutes or ascorbic acid for about 24 hours at about 37° C. with constant shaking. The residual BPL may be removed from the inactivated sample by dialysis against PBS using a 10,000 to 20,000 molecular weight membrane.

Immunogenicity Studies in Cotton Rats

The purified and inactivated RS viral material provided by this procedure is immunogenic and protective while being non-infectious. This result was determined by evaluation of the immunogenicity RS viral materials in cotton rats including their capacity to protect these animals from live RS virus challenge, as reported below. Vaccine preparations provided herein elicited RS virus specific neutralizing antibodies and protected cotton rats from live virus challenge.

It is clearly apparent to one skilled in the art, that the various embodiments of the present invention have many applications in the fields of vaccination, diagnosis, treatment of diseases caused by respiratory syncytial virus and the generation of immunological reagents. A further non-limiting discussion of such uses is further presented below.

Vaccine Preparation and Use

Immunogenic compositions, suitable to be used as vaccines, may be prepared from inactivated RSV as disclosed herein. The vaccine elicits an immune response in a subject which produces anti-RSV antibodies. Should the vaccinated subject be challenged by RSV, the antibodies bind to and inactivate the virus.

Immunogenic compositions including vaccines may be prepared as injectables, as liquid solutions or emulsions. The inactivated RSV may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Methods of achieving adjuvant effect include the use of agents such as aluminum hydroxide or phosphate (alum), commonly used as 0.05 to 0.1 percent solution in phosphate buffered saline. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the inactivated RSV provided herein. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable, but may include an initial administration followed by subsequent administrations. The dosage may also depend on the route of administration and will vary according to the size of the host.

The concentration of inactivated RS virus in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunoassays

The inactivated RSV preparations of the present invention are useful as immunogens for the generation of antibodies (including monoclonal antibodies) specifically reactive with RSV proteins as antigens in immunoassays including enzyme linked immunosorbent assays (ELISA), RIAs and other non-enzyme linked antibody binding assays or procedures known in the art for the detection of bacterial antibodies. In ELISA assays, the inactivated RSV is immobilized onto a selected surface, for example, a surface capable of binding proteins such as the wells of a polystyrene microtiter plate. After washing to remove incompletely adsorbed virus, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound inactivated RSV, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectra spectrophotometer.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for the purpose of limitation.

Methods of determining tissue culture infectious $dose_{50}$ ($TCID_{50}$/mL), plaque and neutralization titres, not explicitly described in this disclosure are amply reported in the scientific literature and well within the scope of those skilled in the art. Protein concentrations were determined by the bicinchoninic acid (BCA) method as described in the Pierce Manual (23220, 23225; Pierce Chemical Company, U.S.A.), incorporated herein by reference.

CMRL 1969 culture media was used for cell culture and virus growth. The cells used in this study are vaccine quality African green monkey kidney cells (VERO lot M6) obtained from Institut Mérieux. The RS viruses used were the RS virus subtype A (Long and A2 strains) obtained from the American Type Culture Collection (ATCC) and a recent subtype A clinical isolates, designated Tracy and RSV-3-D1T. Comparable results were obtained in the following Examples with each RSV.

Example I

This Example illustrates the growth of African green monkey kidney (VERO, lot M6) cells.

African green monkey kidney (VERO) cells were grown on microcarrier beads (Cytodex-1, Pharmacia). The beads used at a concentration of 2.5 g/L, were swollen in phosphate buffered saline (PBS), pH 8.0 in the absence of calcium and magnesium, for 3 hours at room temperature with gentle agitation (50 rpm). After this incubation period, the PBS solution was decanted and the beads were washed once with 1.5 L PBS. The supernatant was decanted and the volume of PBS brought to 2L. The microcarrier beads were sterilized at 121° C. for 45 min and conditioned in CMRL 1969 cell culture medium in a large (40L) fermentor. The culture vessel was seeded ($10^5$ cells/mL) with VERO, M6 cells in CMRL 1969 culture medium supplemented with fetal bovine serum (5 percent final concentration).

Example II

This Example illustrates the growth of RS virus in tissue culture.

Once the cells reached about 90 percent confluency, the culture supernatant was decanted and the cells washed with CMRL 1969 culture medium. The cells were infected with RS virus at a multiplicity of infection (moi) of 0.001 in culture medium free of exogenously-added FBS. The virus was allowed to adsorb to the cells for 1 hour at 37° C. with gentle agitation. After the adsorption period, the cells were washed once with CMRL 1969, and incubated with CMRL 1969 medium. After ten days post-infection, the culture fluid was harvested (Harvest I), processed as described in Example III and stored at −70° C. in the presence of 20% sucrose. CMRL 1969 then was added to the fermentor and the virus-infected cells were incubated for an additional four days to collect a second virus harvest (Harvest II). This second viral harvest then was processed as described in Example III. The titre of infectious virus present in the fluids was monitored by the plaque assay.

Example III

This Example illustrates the processing of RS virus.

The viral fluid from RS virus-infected VERO cells, collected at days 10 and 14 Post-infection (Harvests I and II), were processed separately. Each viral harvest was microfiltered using a 5 μm pore size filter (dead-end filtration) to remove the cell debris. The clarified virus supernatant was further concentrated by tangential flow ultrafiltration (Sartorius) with a membrane of 100 kDa molecular weight cut-off. The RS virus retentate was stored at −70° C.

Example IV

This Example illustrates the concentration of RS virus by ultracentrifugation.

RS virus retentate was centrifuged at 45,000 r.p.m. using a 50.2 Ti Beckman fixed angle rotor, for two hours at 4° C. The supernatant was discarded and the pelleted virus was resuspended in phosphate buffered saline (PBS) pH 7.3.

Example V

This Example illustrates the purification of RS virus by sucrose density gradient centrifugation.

The resuspended pelleted virus was further purified by rate zonal centrifugation (2 hours at 24,000×rpm, Beckman SW 28 rotor) on linear 10–60% (w/v) sucrose gradients. The diffuse viral band harvested from the 35–40% zone was diluted in PBS to a final concentration of 10% sucrose. The purified virus was further concentrated by ultracentrifugation at 45,000 rpm for 90 min. in a Beckman 50.2 Ti rotor. The supernatant was discarded. The pelleted virus was resuspended in PBS to a protein concentration of approximately 1 mg/mL and stored at −70° C. The purified RS virus was analyzed by polyacrylamide gel electrophoresis and immunoblotting using anti-RSV specific antibodies and found to have a purity of at least about 60%, which is considered to be substantially free from cellular and serum components.

Example VI

This Example illustrates purification and concentration of RS virus by gel filtration and chromatography.

Virus retentate from RSV-3-D1T prepared as described in Example III was purified and concentrated by gel filtration and column chromatography as follows:

Virus retentate from Example IV was passed through a gel filtration column (Sephacrye S-500) equilibrated in 10 mM sodium phosphate buffer, pH 7.3, containing 10 mM sodium chloride and 20% glycerol to remove the main contaminant, bovine serum albumin (BSA). The virus was further purified and concentrated on an ion exchange column (DE-52, Whatman) equilibrated in the above buffer. The resin was washed with the equilibration buffer and then with five column volumes of a buffer containing 10 mM sodium phosphate pH 7.3, 100 mM sodium chloride and 20% glycerol. In this step, non-viral components, mainly BSA, still present in the viral fraction purified by gel filtration were eluted. The virus was eluted from the column with 50 mM sodium phosphate and 1.5 M sodium chloride.

Example VII

This Example illustrates the inactivation of RS virus by n-octyl-β-D-glucopyranoside (OG).

RS virus, prepared as described in Examples V and VI, was inactivated by treatment with n-octyl-β-D-glucopyranoside (1% wt/vol) for two hours at room temperature. The viral sample then was dialyzed against phosphate buffered saline to eliminate the detergent from the protein mixture. The infectivity of the inactivated virus was tested by the $TCID_{50}$ assay and no infectious virus was detected.

Example VIII

This Example illustrates the immunogenicity of the n-octyl-β-D-glucopyranoside (OG)-inactivated RS virus preparation.

Six week old cotton rats were injected intramuscularly with 30 μg/kg of either aluminum phosphate adsorbed OG-inactivated RS virus prepared as described in Example VI or irrelevant antigen (placebo). One group of animals was inoculated intranasally with approximately 100 cotton rat infectious doses ($CRID_{50}$) of live RS virus in 100 μL. On day 28, all animals were bled and all but those given live virus were boosted using the same dose of adjuvanted antigen as that used in the primary inoculation. Sera samples also were taken one week after the booster dose (day 35). RS virus specific neutralizing titers were determined and are presented in Table 1 appearing below. (The Tables appear at the end of the descriptive text).

As may be seen from this Table, data from the first bleed (28 days) demonstrated that the OG-inactivated RS virus preparation elicited a strong primary immune response. The sera from animals boosted at 4 weeks with an equivalent dose of the adjuvanted OG-inactivated RS virus had neutralizing antibody titres at day 35 which were comparable to those obtained in the sera of animals which were inoculated with live virus. The data presented herein demonstrates that the OG-inactivated RS virus was highly immunogenic.

Example IX

This Example illustrates the ability of the OG-inactivated RS virus preparation to elicit a protective response in immunized cotton rats without causing enhanced pulmonary pathology.

To evaluate the protective ability of the n-octyl-β-D-glucopyranoside-inactivated RS virus preparation, cotton rats inoculated with either live RS virus or injected with two 30 μg doses of inactivated RS virus or an irrelevant antigen (placebo) were challenged intranasally (7 days after the booster dose) with approximately 100 cotton rat infectious doses ($CRID_{50}$) of the A2 strain of RS virus grown in Hep2 cells. On day 4 after virus challenge, half the animals were killed. Their lungs were removed, lavaged and the resulting fluids assessed for both pulmonary virus titres and leukocyte number (as a measure of lung inflammation). On day 7 after virus challenge, the remaining animals were sacrificed their lungs removed and assessed for virus levels. The presence of lung bronchio lavage cells also was determined. Histopathology was performed on lung sections using hematoxylin and eosin stains of paraffin sections.

The pulmonary RS virus titres on day 4 postchallenge are summarized in Table 2. Placebo control animals injected with an irrelevant protein preparation supported the replication of 6.6 $\log_{10}$ $TCID_{50}$ units of virus per gram of lung tissue. No virus was detected in the lungs of animals immunized with the OG-inactivated RS virus preparation. These results demonstrate the protective ability of OG-inactivated RS virus. RS virus pulmonary titres on day 7 (data not shown) were minimal in all lungs tested. This is not unexpected, since RS virus is normally cleared from the lungs by 7 days post challenge.

Lung lavage cell counts (Table 3) of animals immunized with the OG-inactivated RS virus preparation were significantly lower than cell counts from the lungs of animals inoculated with the irrelevant protein preparation (placebo). Furthermore, cell counts at day 7 from OG-inactivated RS virus inoculated animals were not significantly different than placebo control counts. Since 7 day lung lavage cell counts were not significantly greater than the placebo control counts, it can be concluded that the OG-inactivated RS virus preparation did not cause enhanced lung inflammation in immunized animals following live virus challenge.

Hematoxylin and eosin-stained sections showed that the lungs of animals given the irrelevant protein formulation (placebo) had maximum indications of infection and inflammation while the lungs of cotton rats immunized with either live virus or the OG-inactivated RS virus preparation had minimal evidence of either infection or inflammation. The results are summarized in Table 8.

Based on these results, it can be concluded that the OG-inactivated RS virus preparation can elicit a protective immune response without causing exacerbated pulmonary pathology.

Example X

This Example illustrates the inactivation of RS virus with β-propiolactone (BPL).

The inactivating agent, β-propiolactone (0.1 percent w/v in distilled water) was sterilized by filtration through a 0.22 Am pore size filter. Purified RS virus, prepared as described in Example V, mixed with the inactivating agent in a 1:1 ratio (v/v) and incubated for two hours at 37° C. with constant shaking. This viral sample was further dialyzed overnight at 4° C. against PBS using a 12000 molecular weight cutoff membrane to remove residual BPL. The infectivity of the treated viral sample was evaluated in the plaque assay and no infectious virus was detected. The dialyzed sample was stored at −70° C.

Example XI

This Example illustrates the immunogenicity and protective capability of β-propiolactone-inactivated RS virus and that it did not cause enhanced pulmonary pathology.

Six week old female cotton rats were injected intramuscularly with 10 μg/kg of BPL-inactivated RS virus adsorbed to aluminum phosphate. Placebo control animals were immunized with PBS plus aluminum phosphate. A group of animals also were intranasally instilled with 100 $CRID_{50}$ of RS virus. On day 28, the animals were bled and, with the exception of cotton rats immunized with live virus, boosted with the same dose of the antigen formulation. Sera samples were taken on day 84 and RS virus-specific neutralizing titers were determined. To evaluate the ability of the inactivated RS virus preparation to protect animals from live virus challenge, the cotton rats were challenged intranasally with approximately 100 $CRID_{50}$ of RS virus Tracy isolate harvested from cotton rat lungs. Four days after virus challenge, the animals were sacrificed, their lungs removed, lavaged and the resulting fluids assessed for pulmonary RS virus titres.

RS virus-specific neutralizing titers in the sera of animals immunized with BPL-inactivated RS virus are summarized in Table 4. Results from the first bleed (day 28) demonstrated that the BPL-inactivated RS virus formulation elicited a good primary immune response. Furthermore, the sera from animals boosted at 4 weeks with an equivalent dose of the inactivated RS virus had neutralizing antibody titres which were comparable to those obtained in animals inoculated with live virus.

The BPL-inactivated virus preparation also was effective in protecting cotton rats from challenge with RS virus, as shown by the pulmonary RS virus titres shown in Table 5. Thus, animals immunized with two doses of the EPL-inactivated RS virus preparation were protected from live RS virus challenge. The reduction in lung virus titres was comparable to that seen in cotton rats immunized with live RS virus (0.6 log $_{10}$/g lung).

Enhanced pulmonary pathology for β-propiolactone-inactivated RSV preparation was determined as in Example IX above.

The results obtained from these studies show that BPL-inactivated RS virus is highly immunogenic and protective.

Example XII

This Example describes the inactivation of RS virus with ascorbic acid.

Solutions of (10 mg/mL) ascorbic acid and copper sulfate (0.5 mg/mL) were sterilized by filtration through a 0.22 μm pore size filter. Virus purified as described in Example VI above was mixed with these solutions to give a final concentration of 1 mg/mL ascorbic acid and 50 μg/mL copper sulfate (4 parts of virus and 0.5 parts of each solution) and the mixture was incubated at 37° C. for 24 hours with shaking.

The infectivity of the treated viral sample was evaluated in the plague assay and no infectious virus was detected. The dialyzed sample was stored at −70° C.

Example XIII

This Example describes the immunogenicity and protective capability of the ascorbic acid-inactivated RS virus and that it does not cause enhanced pulmonary pathology.

Cotton rats (5 to 8 weeks old) were injected intramuscularly with 10 μg/kg of ascorbic acid inactivated RSV (AAI-RSV) adjuvanted with aluminum phosphate or with a placebo control (alum plus PBS). Another group of animals was inoculated intranasally with approximately 100 cotton rats infectious doses ($CRID_{50}$) (in 100 μl) of live RS virus. On day 28, all animals were bled and all but those given live viruses were boosted using the same dose of adjuvanted antigen as that used in the primary inoculation. Sera samples also were taken one week after the booster dose (day 35). RS virus-specific neutralizing titers were determined and are presented in Table 6 appearing below.

The results from the first bleed (28 days) shown in this Table, demonstrate that the ascorbic acid inactivated RSV formulation elicited a strong primary immune response. Furthermore, the results obtained after the second immunization, show that the sera of these animals had neutralizing antibody titres which were comparable to those obtained in the sera of the animals inoculated with live virus.

Example XIV

This Example illustrates the ability of the ascorbic acid-inactivated RS virus formulation to elicit a protective response in immunized cotton rats.

Cotton rats were inoculated with either live RS virus or injected with two 10 ug doses of AAI-RSV or an placebo control (PBS+alum). Seven days after the booster dose, the animals were challenged with approximately 100 $CRID_{50}$ of the A2 strain of RS virus grown on Hep2 cells. On day 4 after virus challenge, half the animals were killed. Their lungs were removed, lavaged and the resulting fluids assessed for both pulmonary virus titres. Histopathology was performed as described previously. The pulmonary virus titers in the lung tissue of placebo control animals was found to be 4.0 $\log_{10}$ $TCID_{50}$ units of units per gram of lung tissue (Table 7). No virus was found in the lungs of the cotton rats immunized with the ascorbic acid inactivated RS virus preparation. These results demonstrate the protective ability of the ascorbic acid inactivated RS virus (AAI-RSV) vaccine preparation to protect against RS viral challenge without causing enhanced pulmonary pathology.

RS virus-specific neutralizing titres in the sera of animals immunized with ascorbic acid-inactivated RS virus (AAI-RSV) are summarized in Table 6. Results from the first bleed (day 28) demonstrated that the ascorbic acid-inactivated RS virus formulation elicited a good primary immune response. Furthermore, the sera from animals boosted at 4 weeks, with the inactivated vaccine had neutralizing antibody titres which were comparable to those obtained in animals inoculated with live virus.

The ascorbic acid-inactivated virus preparation also was effective in protecting cotton rats from challenge with RS virus, as shown by the pulmonary RS virus titres shown in Table 7. Thus, animals immunized with two doses of the ascorbic acid-inactivated RS virus preparation were protected from live RS virus challenge. The reduction in lung virus titres was comparable to that seen in cotton rats immunized with live RS virus and no virus was recovered.

Based on this data, it is suggested that the AAI-RSV formulation can elicit a virus specific neutralizing antibody in the sera of the immunized animals and protect the cotton rats from live virus challenge.

SUMMARY OF DISCLOSURE

In summary of this disclosure, the present invention provides a novel immunogenic composition capable of producing a RS virus specific immune response in a host immunized therewith, comprising purified inactivated RS virus and methods of preparation and utilizing the same. Modifications are possible within the scope of the invention.

TABLE 1

RS virus neutralizing antibody titres in the sera of cotton rats immunized with OG-inactivated RS virus.

| Immunogen | Virus neutralizing titre ($log_2$/0.05 mL)[1] 28 days post-Immunization | 35 days post-immunization |
|---|---|---|
| Placebo | 0.0(0.0) | 0.0(0.0) |
| Live RS virus | 4.0(0.0) | 4.2(1.1) |
| OG inactivated RS virus | 4.0(0.7) | 4.4(0.5) |

[1]values are GMT of 4 samples and standard deviations are shown in brackets ( ).

TABLE 2

RS virus titres in lungs of cotton rats immunized with OG-inactivated RS virus.

| Immunogen | Pulmonary virus titre (GMT log/10 g lung ± S.D.)[1] | p Value (t test) |
|---|---|---|
| Placebo | 4.6(0.5) | — |
| Live RS virus | 1.5(1.0) | <0.001 |
| OG inactivated RS virus | 1.0(0.0) | <0.001 |

[1]values are GMT of 4 samples and standard deviations are shown in brackets ( ).

TABLE 3

Lung cell counts obtained from bronchio lavage fluids of cotton rats immunized with OG-inactivated RS virus and challenged with RS virus.

| Immunogen | Lung cell counts[1] 4 days post challenge | 7 days challenge |
|---|---|---|
| Placebo | 24(5) | 27(14) |
| Live RS virus | 2(1) | 9(2) |
| OG inactivated RS virus | 6(2) | 30(17) |

[1]values are GMT of 4 samples and standard deviations are shown in brackets ( ).

TABLE 4

RS virus neutralizing antibody titres in the sera of cotton rats immunized with β-propiolactone-inactivated RS-virus

| Immunogen | Virus neutralizing titre ($log_2$/0.05 mL)[1] 28 days post-immunization | 84 days post-immunization |
|---|---|---|
| Placebo | 2.5(0.60) | 1.3(1.2) |
| Live RS virus | 7.7(1.2) | 6.7(0.6) |
| BPL-inactivated RS virus | 5.0(0.7) | 6.0(0.0) |

[1]values are GMT and standard deviations are shown in brackets ( ).

TABLE 5

RS virus titres in lungs of cotton rats immunized with β-propiolactone-inactivated RS virus.

| Immunogen | Pulmonary virus titre[1] |
|---|---|
| Placebo | 4.3(0.5) |
| Live RS virus | 0.6(1.0) |
| BPL-inactivated RS virus | 0.6(1.0) |

[1]values are GMT and standard deviations are shown in brackets ( ).

TABLE 6

RS virus neutralizing antibody titres in the sera of cotton rats immunized with ascorbic acid-inactivated RS virus.

| Immunogen | Virus neutralizing titre ($log_2$/0.05 mL)[1] 28 days post-immunization | 35 days post-immunization |
|---|---|---|
| Placebo | 2.6(0.5) | 2.4(0.5) |
| Live RS virus | 9(0) | 8.8(0.5) |
| Ascorbic acid-inactivated RS Virus | 8.6(0.6) | 8.4(0.6) |

[1]values are GMT of 4 samples and standard deviations are shown in brackets ( ).

TABLE 7

RS virus titres in lungs of cotton rats immunized with ascorbic-acid inactivated RS virus.

| Immunogen | Pulmonary virus titre (GMT log/10 g lung ± S.D.)[1] |
|---|---|
| Placebo | 4 ± 0.27 |
| Live ES virus | 0 ± 0 |
| Ascorbic acid-inactivated virus | 0 ± 0 |

[1]values are GMT of 6 samples and standard deviations are shown in brackets ( ).

REFERENCES

1. Glezen, W. P., Paredes, A. Allison, J. E., Taber, L. H. and Frank, A. L. (1981). J. Pediatr. 98, 708–715.
2. Chanock, R. M., Parrot, R. H., Connors, M., Collins, P. L. and Murphy, B. R. (1992) Pediatrics 90, 137–142.
3. Martin, A. J., Gardiner, P. S. and McQuillin, J. (1978). Lancet ii, 1035–1038.
4. Robbins, A., and Freeman, P. (1988) Sci. Am. 259, 126–133.

5. Glezen, W. P., Taber, L. H., Frank, A. L. and Kasel, J. A. (1986) Am. J. Dis. Child. 140, 143–146.

6. Katz, S. L. New vaccine development establishing priorities. Vol. 1. Washington: National Academic Press. (1985) pp. 397–409.

7. Wertz, G. W., Sullender, W. M. (1992) Biotech. 20, 151–176.

8. McIntosh, K. and Chanock, R. M. (1990) in Fields Virology (Fields, B. M., and Knipe, D. M. eds.) pp. 1045–1075, Raven Press, Ltd., New York.

9. Walsh, E. E., Hall, C. B., Briselli, M., Brandiss, M. W. and Schlesinger, J. J. (1987) J. Infect. Dis. 155, 1198–1204.

10. Walsh, E. E., Hruska, J. (1983) J. Virol. 47, 171 177.

11. Levine, S., Kleiber-France, R., and Paradiso, P. R. (1987) J. Gen. Virol. 69, 2521–2524.

12. Anderson, L. J., Hierholzer, J. C., Tsou, C., Hendry, R. M., Fernie, B. F., Stone, Y. and McIntosh, K. (1985), J. Infect. Dis. 151, 626–633.

13. Johnson, P. R., Olmsted, R. A., Prince, G. A., Murphy, B. R., Alling, D. W., Walsh, E. E. and Collins, P. L. (1987) J. Virol. 61 (10), 3163–3166.

14 Fulginiti, V. A., Eller, J. J., Sieber, O. F., Joyner, i. W., Minamitani, M. and Meiklejohn, G. (1969) Am. J. Epidemiol. 89 (4), 435–448.

15. Chin, J., Magoffin, R. L., Shearer, L. A., Schieble, J. H. and Lennette, E. H. (1969) Am. J. Epidemiol. 89 (4), 449–463.

16. Kapikian, A. Z., Mitchell, R. H., Chanock, R. M., Shvedoff, R. A. and Stewart, C. E. (1969) Am. J. Epidemiol. 89 (4), 405–421.

17. Kim, H. W., Arrobio, J. O., Pyles, G., Brandt, C. D Camargo, E., Chanock, R. M. and Parrott, R. H. (1971 Pediatrics 48, 745–755.

18. Wright, P. F., Belshe, R. B., Kim, H. W., Van Voris, L. P. and Chanock, R. M. (1982) Infect. Immun. 37 (1), 397–400.

19. Wright, P. F., Chinozaki, T. and Fleet, W. (1976) J. Pediatr. 88, 931–936.

20. Belshe, R. B., Van Voris, L. P. and Mufson, M. A. (1982) J. Infect. Dis. 145, 311–319.

21. Murphy, B R., Prince, G. A., Walsh, E. E, Kim H. W., Parrott, R. H., Hemming V. G., Rodriguez, W. J., and Chanock. J. Clin. Microbiol. (1986), 24 (2), 197–202.

22. Connors, M., Collins, P. L., Firestone, C- Y., Sotnikov, A. V., Waitze, A., Davis, A. R., Hung, P. P., Chanock, R. M., Murphy, B. (1992) Vaccine, 10, 475–484.

23. Prince, G. A., Jenson, A. B., Hemming, V. G., Murphy, E. R., Walsh, E. E., Horswood, R. L and Chanock, R. L. (1986 b) J. Virol. 57 (3), 721–728.

24. Piedra, P. A., Camussi, F. and Ogra, P. L. (1989) J. Gen. Virol. 70, 325–333.

25. Walsh, E. E., Hall, C. B., Briselli, M., Brandiss, M. W. and Schlesinger, J. J. (1987) J. Infect. Dis. 155 (6), 1198–1204.

26. Budowsky, E. I. and Zheleznova, N. V. (1991) Vaccine 9 (6), 319–325.

27. Budowsky, E. I., Friedman, E. A., Zheleznova, N. V. and Noskov, F. S. (1991) Vaccine 9 (6), 398–402.

28. Stephan, W., Dichtelmuller, H., Prince, A. M., Brotman, B. and Huima, T. J. Med. Virol. (1988), 26 (3), 227–232.

29. Barth, R., Gruschkau, H., Bijok, U., Hilfenhaus, J., Hinz, J. and Milcke, L. J. Biol. Stand. (1984), 12 (1), 29–46.

30. Salkind, A. R. and Roberts N. J. (1992) Vaccine. 10, 519–523.

31. Murphy, B. R., Prince, G. A., Collins, P. L. Coelingh, K. V. W., Olmsted R. A., Spriggs, M. K., Parrott, R. H., Kim, H- W., Brandt, C. D. and Chanock, R. M. (1988) Virus Research 11, 1–15.

32. Kimman, T. G. and Westenbrink, F. (1990) Archives of Virology 112, 1–25.

33. Wertz, G. W. and Sullender, W. M. (1992) Biotechnology 20: 151–176.

34. La Via, W. V., Marks, M. I., Stutman H. R. (1992) J. Pediatrics 121, 503–510.

We claim:

1. A method of preparing a non-immunopotentiating, vaccine composition capable of protecting a human host immunized therewith against disease caused by infection by respiratory syncytial (RS) virus, which comprises:

growing RS virus on a continuous cell line of vaccine quality in the presence of microcarrier beads to produce a grown virus;

harvesting said growth virus by collecting culture fluid to produce a harvested virus;

purifying said harvested virus under non-denaturing conditions to produce a purified virus free from cellular and serum components;

inactivating said purified virus with an inactivating agent selected from the group consisting of β-propiolactone, a non-ionic detergent which is n-octyl-α-D-glucopyranoside or n-octyl-β-D-glucopyranoside, and ascorbic acid to provide a non-infectious, non-immunopotentiating and protective RS viral preparation, and formulating said non-infectious, non-immunopotentiating and protective RS viral preparation as a vaccine.

2. The method of claim 1 wherein said continuous cell line is a VERO cell line.

3. A method of preparing a non-immunopotentiating vaccine capable of protecting a human host immunized therewith against disease caused by infection by respiratory syncytial (RS) virus, which comprises:

growing RS virus on a continuous cell line of vaccine quality in the presence of microcarrier beads to produce a grown virus;

harvesting said growth virus by collecting culture fluid to produce a harvested virus;

purifying said harvested virus under non-denaturing conditions to produce a purified virus free from cellular and serum components by:

(i) microfiltration to remove cell debris, (ii) tangential flow ultrafiltration to remove serum components and provide a retentate, (iii) pelleting the retentate by ultracentrifugation to further remove serum components, and (iv) subjecting the pelleted material to sucrose density gradient centrifugation;

inactivating said purified virus with an inactivating agent selected from the group consisting of β-propiolactone, a non-ionic detergent which is n-octyl-α-D-glucopyranoside or n-octyl-β-D-glucopyranoside, and ascorbic acid, to provide a non-infectious, non-immunopotentiating and protective RS viral preparation, and formulating said non-infectious, non-immunopotentiating and protective RS viral preparation as a vaccine.

4. The method of claim 3 wherein said tangential flow ultrafiltration is effected by employing an about 100 to about 300 kDa nominal molecular weight cut off membrane.

5. A method of preparing a non-immunopotentiating vaccine capable of protecting a human host immunized therewith against disease caused by infection by respiratory syncytial (RS) virus, which comprises:

growing RS virus on a continuous cell line of vaccine quality in the presence of microbeads to produce a grown virus;

harvesting said growth virus by collecting culture fluid to produce a harvested virus;

purifying said harvested virus under non-denaturing conditions to produce a purified virus free from cellular and serum components by:

(i) microfiltration to remove cell debris, (ii) tangential flow ultrafiltration to remove serum components, (iii) gel filtration to further remove serum components, and (iv) ion-exchange chromatography to additionally remove serum components;

inactivating said purified virus with an inactivating agent selected from the group consisting of β-propiolactone, a non-ionic detergent which is n-octyl-α-D-glucopyranoside or n-octyl-β-D-glucopyranoside, and ascorbic acid, to provide a non-infectious, non-immunopotentiating and protective RS viral preparation, and formulating said non-infectious, non-immunopotentiating and protective RS viral preparation as a vaccine.

* * * * *